United States Patent [19]

Gibbs

[11] 4,331,467

[45] May 25, 1982

[54] NOVEL THIOUREIDOIMINOISOINDOLINONE AND USE AS PLANT GROWTH REGULATOR

[75] Inventor: Charles G. Gibbs, Shawnee Mission, Kans.

[73] Assignee: Gulf Oil Corporation, Pittsburgh, Pa.

[21] Appl. No.: 136,853

[22] Filed: Apr. 3, 1980

[51] Int. Cl.³ .................... A01N 43/38; E07D 209/50
[52] U.S. Cl. ........................................... 71/96; 71/76; 548/471
[58] Field of Search ................... 71/96, 76; 260/326.1, 260/395 PH

[56] References Cited

U.S. PATENT DOCUMENTS 4,264,502  4/1981  Patel et al. .............................. 71/96

*Primary Examiner*—Catherine L. Mills
*Attorney, Agent, or Firm*—Deane E. Keith; Forrest D. Stine; Carl A. Cline

[57] ABSTRACT

A new substance which is useful as a plant growth regulator is 3-imino-2-(1-methyl-3-phenylthioureido)isoindolin-1-one, which may also exist in tautomeric form as 1-(2-cyanobenzoyl)-2-methyl-4-phenylthiosemicarbazide. Formative effects and increased fruit set are obtained by application of the growth regulator to crop plants.

6 Claims, No Drawings

NOVEL THIOUREIDOIMINOISOINDOLINONE AND USE AS PLANT GROWTH REGULATOR

DESCRIPTION OF THE INVENTION

This invention is directed to a novel compound having the structural formula

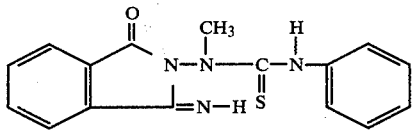

which may also exist in tautomeric form, as discussed below. This substance has an extraordinarily high degree of activity as a plant growth regulator, being capable of inducing increased fruit set in some crop plants when applied to the plants at rates of one ounce per acre (70 g per hectare) or less.

Although various substituents may be present on the aromatic rings without disappearance of the growth regulator effect, the additional expense of making the more complex compounds is not offset by adequate beneficial characteristics. The simple compound, without substitution on the aromatic rings is therefore preferred, rather than more complex compounds, which, at best, are no more than equivalent as growth regulators.

If desired, the growth regulator may also be converted to an isothiuronium salt form, by conventional methods, so as to make it easier to formulate in water-soluble or water-dispersible agricultural compositions. The method of regulating growth of plants with the novel compound includes the use of the compound in the form of its agriculturally acceptable isothiuronium salts, as well as in tautomeric form or salts thereof.

SYNTHESIS OF THE GROWTH REGULATOR

The new composition may be synthesized by the route outlined below:

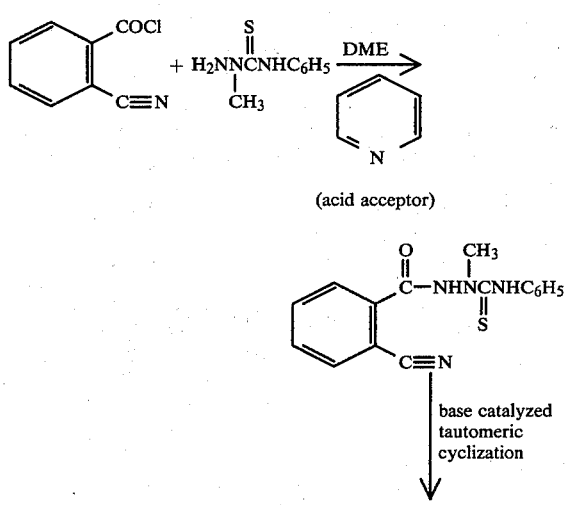

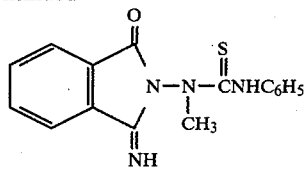

The 2-Cyanobenzoylchloride is prepared as taught by W. L. Armarego and S. C. Sharma, J. Chem. Soc. (C), 1600 (1970).

The 2-Methyl-4-phenylthiosemicarbazide (or 1-methyl-N-phenylhydrazinethiocarboxamide) is prepared as follows:

To a solution of N-phenylthiocarbamyl chloride 73.7 g (0.43 m) in 250 ml dry ether, a solution of 39.5 g (0.86 m) methylhydrazine in 100 ml of dry ether is added dropwise with stirring below 10° C. The reaction temperature is allowed to increase to room temperature and the mixture is filtered. The filtrate is evaporated to low volume and diluted with ~300 ml hexane. After stirring for a few hours the hexane layer is decanted. The hexane immiscible layer is reevacuated to remove organic solvents, giving the desired product as a viscous liquid.

Preparation of the tautomeric compound, according to the above schedme, is illustrated below:

EXAMPLE I

Preparation of 3-Imino-2-(1-methyl-3-phenylthioureido)isoindolin-1-one

A solution of crude 2-cyanobenzoylchloride (2.2 g; 0.013 mole) in 20 ml of dimethoxyethane was added dropwise to a solution of 2-methyl-4-phenylthiosemicarbazide 0.35 g; 0.013 mole) and pyridine (1.1 g; 0.013 mole) in 35 ml of dimethoxyethane. The resulting red solution was allowed to stir at room temperature overnight. The reaction mixture was poured into a large volume of water to give a reddish gummy precipitate. The water was decanted and the gummy material dissolved in a small amount of ethyl acetate. Upon standing a solid crystallized from solution. Filtration gave 1 g of the desired product, mp: 165-167. The IR and NMR spectra were consistent with the cyclic tautomer structure, as illustrated in the foregoing reaction scheme. Under basic conditions, as in the exemplified synthesis procedure, existence of the tautomeric ortho-cyanobenzoyl compound is probably negligible. It is conceivable, however, that in some chemical environments the tautomeric form can be detected, or that reaction products derived from the tautomeric form will be produced when identification by preparation of chemical derivatives is attempted.

USE OF THE GROWTH REGULATOR

The effects of this novel compound as a growth regulator, resulting from both pre-emergent and post-emergent application is readily apparent. These effects may be demonstrated by means of the following illustrative procedures.

PRE-EMERGENT APPLICATION

Disposable paper trays about 2½ inches deep were filled with soil and sprayed with aqueous spray mixtures at a rate of 5 lb. of active chemical per acre of sprayed area, were seeded with 6 species of plant seeds and were then covered with about ¼ inch of soil. The spray mixtures were prepared by dissolving the proper amount of growth regulator compound in 15 ml of acetone, adding 4 ml of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 60 ml by addition of warm water. Twenty-one days after seeding and treatment the plantings were examined and plant injury was rated according to the following schedule:

DEGREE OF EFFECT

0 = no effect
1 = slight effect, plants recovered
2 = moderate effect, injury to 26 to 75 percent
3 = severe effect, injury to 76 to 93 percent of foliage
4 = maximum effect (all plants died)

POST-EMERGENT APPLICATION

Several species of plants were grown in potting soil in disposable styrofoam trays and tomatoes were grown in four-inch pots in the greenhouse. Aqueous spray formulations were prepared and the growing plants were sprayed at a spray volume of 60 gallons per acre and an application rate of 5 lb. per acre. Spray mixtures were prepared in the manner described above. For comparative purposes, plants were also sprayed at 60 gal./acre with a spray mixture containing no growth regulator. Plant injury was again rated according to the schedule disclosed above and observations of growth regulator effects were observed and recorded as follows; for both pre- and post-emergent applications:

| Effect | Abbreviation in Tables |
| --- | --- |
| Formative effect on new growth | F |
| Epinasty | E |
| Growth reduction | G |
| Non-emergence | K |
| Necrosis | N |

In Table I below there are tabulated the observations of pre- and post-emergent herbicidal and growth regulator effects of various compounds disclosed above.

TABLE I

| EFFECTS ON NINE SPECIES | | |
| --- | --- | --- |
| Species | Pre | Post |
| Crabgrass | 0 | — |
| Coxcomb | F1 | — |
| Brome | F2G2 | — |
| Millet | F1G1 | F2G1 |
| Alfalfa | — | F3G3 |
| Oats | — | F2G1 |
| Radish | F1G1 | F1 |
| Sugar Beet | F2G2 | F2G1 |
| Tomato | — | F3G1 |

The use of the growth regulator compound may be demonstrated by treatment of soybeans (*Soja max*) to increase the number of seed pods and by treating tomato plants (*Lycopersicum esculentum*) to increase fruit set. In an illustrative experiment, *Soja max* (Evans variety) and *Lycopersicum esculentum* (Tiny Tim variety) were grown in 4-inch pots (one plant per pot) filled with greenhouse potting soil (2 parts good top soil, 1½ parts builders' sand, 1½ parts peat, fertilized with 5 lb. of 12-12-6 fertilizer and 5 lb. of finely ground limestone per cu. yd.). Aqueous spray formulations were prepared and the potted plants were sprayed at a spray volume of 40 gal. per acre and at application rates of 16, 4, 1 and ¼ oz. per acre. The spray mixtures were prepared by dissolving the proper amount of growth regulator compound in 15 ml. of acetone, adding 2 ml. of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 80 ml by addition of a 0.156 wt. percent aqueous solution of liquid non-ionic dispersant (90 wt. percent active trimethylnonyl polyethylene glycol ether, Tergitol TMN-10). Two replicates were sprayed at all application rates. For comparative purposes, plants were also sprayed at 40 gal./acre with water. The number of seed pods and of fruits on both treated and on untreated plants was observed within approximately three weeks after spray treatment and the results are tabulated below as averages of two replicates. The fruit set is expressed as percentage of average pod or fruit count on treated plants, in comparison with average count on untreated plants. The severity of growth regulatory effect on the plants was estimated on a scale of 0 to 10 and is also recorded in the following table:

TABLE II

| GROWTH REGULATING EFFECTS ON TWO SPECIES | | |
| --- | --- | --- |
| Rate (oz./A) | Growth Regulant Effect (0-10 scale) | Fruit Set (% of check) |
| *Lycopersicum esculentum* | | |
| 16 | 8 | 141 |
| 4 | 3 | 169 |
| 1 | 1 | 178 |
| *Soja max* | | |
| 16 | 4.5 | 146 |
| 4 | 1 | 139 |
| 1 | 1 | 105 |

The information presented in tabular form herein will enable a worker in the art to make a selection with regard to application rates, depending upon the effect which is desired. It may be seen, for example, that severe effects on some species of vegetation may occur at application rates of only 5 lb. per acre, whereas beneficial effects may be observed on living plants at application rates of 1 lb. per acre or less.

The growth regulator compound is usually employed in compositions containing from 0.1 to 95 weight percent active ingredient in combination with from 0.1 to 75 weight percent of a surface active agent and inert carriers or diluents, as in emulsifiable concentrates, granules and dust formulations, in accordance with established practice in the art. An aqueous spray is usually prepared by mixing a wettable powder or emulsifiable formulation of a growth regulator with a relatively large amount of water to form a dispersion.

Wettable powders comprise intimate, finely divided mixtures of growth regulator compounds, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the growth regulator compound comprise in each instance, a solution of growth regulator compound in a liquid carrier which is a mixture of water-immiscible solvent and surfactants, including emulsifiers. Useful solvents include aromatic hydrocarbon solvents, such as the xylenes, alkylnaphthalenes, petroleum distillates, terpene solvents, etheralcohols and organic ester solvents. Suitable emulsifiers, dispersing and wetting agents may be selected from the same classes of products which are employed in formulating wettable powders.

I claim:

1. 3-Imino-2(1-methyl-3-phenylthioureido)isoindolin-1-one.

2. An agricultural growth regulator composition comprising from 0.1 to 95 weight percent of the compound of claim 1 and from 0.1 to 75 weight percent of a surface active agent, in combination with an inert carrier.

3. The method of regulating growth of plants comprising applying to the plants, either pre- or post-emergently an effective amount of the composition of claim 2.

4. The method of increasing fruit set of crop plants by applying to the plant foliage an effective amount of the compound of claim 1 in combination with a surface active agent and an inert carrier.

5. The method of claim 4 in which the crop plants are of the species *Lycopersicum esculentum*.

6. The method of claim 4 in which the crop plants are of the species *Soja max*.

* * * * *

UNITED STATES PATENT OFFICE
CERTIFICATE OF CORRECTION

Patent No. 4,331,467　　　　　　　　　Dated May 25, 1982

Inventor(s) Charles G. Gibbs

It is certified that error appears in the above-identified patent and that said Letters Patent are hereby corrected as shown below:

Column 2, line 37, "0.35" should read --(2.35--.

Signed and Sealed this

Ninth Day of November 1982

[SEAL]

Attest:

GERALD J. MOSSINGHOFF

Attesting Officer　　　Commissioner of Patents and Trademarks